United States Patent [19]

End et al.

[11] Patent Number: 5,700,471
[45] Date of Patent: Dec. 23, 1997

[54] PRODUCTION OF FINE PARTICLE DYE OR DRUG PREPARATIONS

[75] Inventors: Lutz End, Mannheim; Dieter Horn, Heidelberg; Erik Lueddecke, Mutterstadt, all of Germany

[73] Assignee: BASF Aktiengesellschaft, Ludwigshafen, Germany

[21] Appl. No.: 573,876

[22] Filed: Dec. 18, 1995

Related U.S. Application Data

[63] Continuation of Ser. No. 298,304, Sep. 1, 1994, abandoned.

[30] Foreign Application Priority Data

Sep. 1, 1993 [DE] Germany .......................... 43 29 446.4

[51] Int. Cl.$^6$ .................. A61K 9/10; A61K 9/14; B01J 13/00; C09B 69/46
[52] U.S. Cl. .................. 424/400; 8/526; 34/372; 252/303; 252/314; 252/363.5
[58] Field of Search ............ 252/303, 314, 252/363.5; 264/4.6; 427/2, 22, 213.35; 424/492, 400; 34/372; 8/526

[56] References Cited

U.S. PATENT DOCUMENTS

| | | | |
|---|---|---|---|
| 2,021,143 | 11/1935 | Calcott et al. | 252/314 |
| 2,332,934 | 10/1943 | Rollo et al. | 252/314 X |
| 3,202,731 | 8/1965 | Grevenstuk et al. | 264/4.6 X |
| 3,461,080 | 8/1969 | Eller et al. | 252/363.5 |
| 3,998,753 | 12/1976 | Antoshkiw et al. | 252/363.5 X |
| 4,144,025 | 3/1979 | Swank | 252/314 X |
| 4,540,602 | 9/1985 | Motoyama et al. | 252/353.5 X |
| 4,844,934 | 7/1989 | Lueddecke et al. | 252/314 X |
| 5,133,908 | 7/1992 | Stainmesse et al. | 264/4.1 |

FOREIGN PATENT DOCUMENTS

| | | |
|---|---|---|
| 0 065 193 | 11/1982 | European Pat. Off. |
| 0 169 618 | 1/1986 | European Pat. Off. |

OTHER PUBLICATIONS

Rose et al.: *The Condensed Chemical Dictionary*, Sixth Edition, Reinhold Publ. Corp., New York (1961) pp. 1091 & 1092.

*Primary Examiner*—Richard D. Lovering
*Attorney, Agent, or Firm*—Oblon, Spivak, McClelland, Maier & Neustadt, P.C.

[57] ABSTRACT

Process for the production of fine-particle, essentially amorphous dye or drug preparations by converting a relatively coarse-particle dispersion or a solution into a colloidal dispersion in water, where the colloidal dispersion is generated at a temperature above the melting point of the dye or drug by admixing appropriately hot water (where appropriate under pressure) or an aqueous protective colloid solution so that an emulsion of a melt in aqueous medium is produced and is immediately spray-dried or converted by cooling into a suspension.

4 Claims, 2 Drawing Sheets

PRODUCTION OF FINE PARTICLE DYE OR DRUG PREPARATIONS

This application is a continuation of application Ser. No. 08/298,304, filed on Sep. 1, 1994, now abandoned.

DESCRIPTION

The present invention relates to an improved process for the micronization of compounds which have low solubility in water.

Various processes exist for producing small particles of compounds which have low solubility in water, as are required to increase the bioavailability of drugs which have low solubility, or the coloring strength of dyes which have low solubility. Thus, for example, EP 65 193, EP 169 618 and U.S. Pat. No. 5,133,908 describe processes in which the drug or dye is converted into a molecular solution in a water-miscible solvent and subsequently reprecipitated in fine-particle form by adding the solution to water or vice-versa. However, these processes have the disadvantage that it is necessary to use relatively large amounts of solvent to dissolve the drug or dye (which is often of low solubility in organic solvents too) to formulate it in fine-particle form.

It is an object of the present invention to minimize the amount of solvent used while still obtaining extremely fine-particle formulations of the dyes and drugs.

This reduction in the amount of solvent is achieved in the procedure according to the invention because it is unnecessary to prepare an intermediate molecular solution of the drug or dye in a water-miscible solvent, on the contrary the process entails the drug or dye which is dispersed in aqueous or organic phase being briefly exposed with vigorous turbulence to a temperature above its melting point, and the resulting fine-particle emulsion is subsequently converted by rapid cooling below the melting point into a stable dispersion of the solid in water. This dispersion can subsequently be concentrated and dried in a conventional way, or the emulsion can be spray-dried immediately, without previous cooling. The result in both cases is a powder which on redispersion in water affords a fine-particle dispersion of the dye or drug.

BRIEF DESCRIPTION OF THE DRAWINGS

FIG. 1 shows an embodiment wherein water is mixed with a dye or drug preparation at a temperature above the melting point of the dye or drug, a protective colloid solution being subsequently added.

FIG. 2 shows an embodiment wherein a dye or drug preparation and a protective colloid solution are mixed at a temperature above the melting point of the drug or dye.

Figure 1:
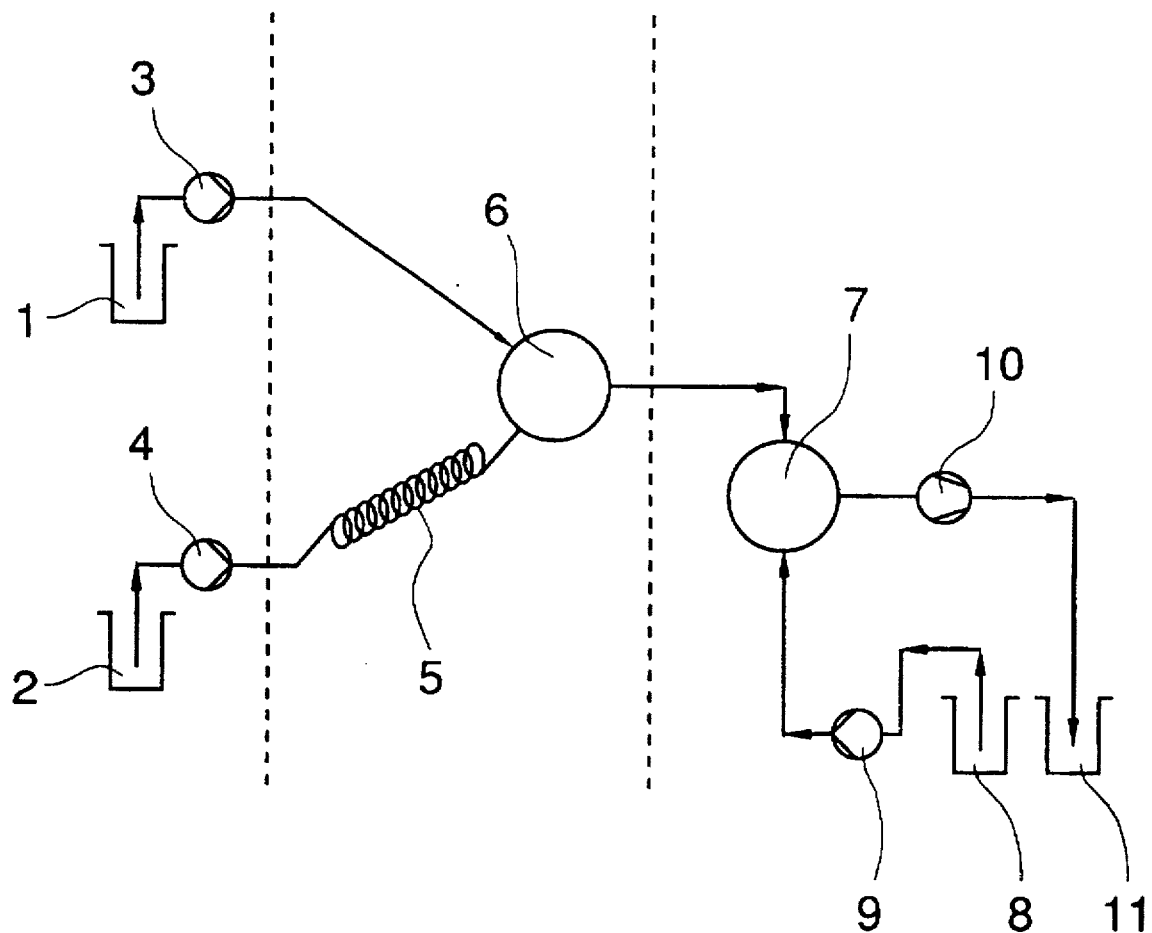
FIGS. 1 and 2 diagrammatically illustrate the production of the micronizate according to the invention.

The avoidance or the reduction of the need for solvents during the formulation not only has the advantage of reduced costs but also makes it possible for the first time to produce stable nano-particles, for example of fenofibrate, because when solid particles are produced via aqueous dispersions they immediately grow, by Ostwaldt ripening, into larger particles and thus the result of the micronization is nullified. Ostwaldt ripening is not observed with the emulsions which are produced briefly as intermediates in this process. It is additionally slowed down by the complete or substantial avoidance of a solvent (and the resulting reduction in the residual solubility in the dispersing medium) to such an extent that no particle growth is observable during the immediate spray drying.

However, there are substances which are not amenable to processing entirely without solvents because their aqueous dispersions agglomerate and therefore cannot be metered. Fenofibrate is one example of this. Substances of this type are therefore, according to the invention, not dispersed in water but dissolved (if they are readily soluble in the relevant solvent) or dispersed in the minimal amount of organic solvent. Complete dissolution is unnecessary; it is sufficient if the suspension can be metered. Then, with vigorous turbulence and, where appropriate, under pressure, water or an aqueous protective colloid solution at a temperature above the melting point of the particular substance is added to this solution or suspension, and the remainder of the process is carried out as described previously, ie. immediate spray drying of the melt emulsion or rapid cooling of the resulting fine-particle emulsion and, where appropriate, dehydration and drying of the resulting suspension. The rapid cooling can expediently be achieved by adding cold water.

The way the turbulence is generated on admixing the water or the aqueous protective colloid solution to the suspension or solution of the dye or drug is unimportant. Vigorous stirring or shaking are possible, for example. It is simplest, and therefore preferred, to inject one or, better, both components in a compact stream so that there is immediate intimate mixing without mechanical aids.

"Fine-particle" or "colloidal dispersion" means particle sizes below 1.5, preferably below 1, μm.

"Essentially amorphous" means that more than one half, preferably more than 70, in particular approximately 100, % of the product produced according to the invention is X-ray amorphous.

The invention is even more important for drugs than for dyes, because for dyes the invention "only" has the advantage that, because of the finer dispersion, the same coloring effect is achieved with less dye, whereas what especially matters for drugs is the improvement in the absorbability when the solubility is low or zero, which is crucial for the effect.

The temperature range suitable for the mixing is from 40° to 250°, preferably from 60° to 200° C.

Protective colloids serve to stabilize the initially formed emulsion and the dispersion produced therefrom by cooling. In addition, they ensure the easy redispersibility of the powder produced according to the invention where appropriate. Examples of protective colloids are gelatins of various origin, casein, gum arabic, lysalbinic acid, starch, dextrin, pectin, methylcellulose, carboxymethylcellulose, hydroxypropylcellulose, alginates, polyvinyl alcohol, polyvinylpyrrolidone and polyacrylates.

"Relatively coarse-particle" means coarse-particle in relation to the final product. The particle size is virtually unimportant and can be in the range from about, 1 to 2000 μm.

Suitable solvents are in principle all those which dissolve to the extent of at least 10% in water. They must also be distillable without decomposition. Examples which may be mentioned are: alcohols, ethers, ketones, esters, acetals, dimethylformamide, N-methylpyrrolidone and dimethyl sulfoxide.

To increase the mechanical stability of the final product it is expedient to add to the colloid a plasticizer or filler such as sugar or sugar alcohols, eg. sucrose, glucose, lactose, invert sugar, sorbitol, mannitol or glycerol.

When the final product is in the form of a dry powder it contains from 0.5 to 20, preferably about 10, % by weight of the dye or drug of low solubility, from 10 to 50% by weight of protective colloid and from 30 to 80% by weight of a plasticizer and, where appropriate, small amounts of other aids such as emulsifiers, antioxidants and other stabilizers.

When an organic solvent is used it can be removed in a conventional way depending on the boiling point, eg. by distillation, where appropriate under reduced pressure, or by extraction with a water-immiscible solvent. In the latter case it has proved possible and expedient to employ the azeotrope which is obtained on use of isopropanol, without removing water, directly as solvent. However, removal preferably takes place together with the removal of water by spray drying or spray granulation.

The resulting dry powder can, when a water-soluble protective colloid is used, be redissolved in water to result in a uniform fine dispersion of the drug in the range of particle size <1 μm.

The resulting drug hydrosole proves, despite the fine dispersion, to be extremely stable in the photochemical stability test.

Examples of suitable dyes and drugs are carotenoids, verapamil, anipamil, propafenone and biperidene.

The parts specified in the examples are by weight.

EXAMPLE 1

Solvent-free micronization of β-carotene

Dye dispersion:

21 parts of β-carotene and 2.3 parts of ascorbyl palmitate were dispersed in 240 parts of water using a magnetic stirrer.

Protective colloid solution:

57.9 parts of gelatin type B, 100 Bloom, and 97.5 parts of lactose were dissolved in 4000 parts of water at 70° C. The resulting solution was cooled to 25° C.

The production of the micronisate is depicted diagrammatically in FIG. 1. The dye dispersion (1) was pumped by the pump (3) at a rate of 230 parts/hour into the first mixing cell (6) where it was mixed with a stream of 4740 parts of water, which had previously been heated to 227° C. by the thermostat (5), per hour from vessel (2) via pump (4). The mixing with the hot water resulted in the mixture abruptly reaching 217° C., which exceeds the melting point of β-carotene (184° C.). After 0.5 s at 217° C., the resulting β-carotene emulsion was mixed in the second mixing cell (7) with the protective colloid solution (8) which was pumped by pump (9) at a flow rate of 32,200 parts/hour. The resulting fine-particle micronisate was discharged through the pressure-limiting valve (10). The β-carotene particles produced in this way have an average size of 576 nm (determined by photon correlation spectroscopy) and were in the form of a colloidally stable dispersion.

EXAMPLE 2

Production of a micronisate of fenofibrate from an emulsion with a solids content of 30%

Drug solution:

500 parts of fenofibrate were dissolved in 1500 parts of isopropanol at 50° C.

Protective colloid solution:

125 g of ascorbyl palmitate were dissolved by stirring in 10,000 parts of water at 70° C. and pH 9 (addition of 1M sodium hydroxide solution). 2000 parts of gelatin type B, 30 Bloom, and 2875 parts of lactose were dissolved by stirring in the resulting solution.

Figure 2:
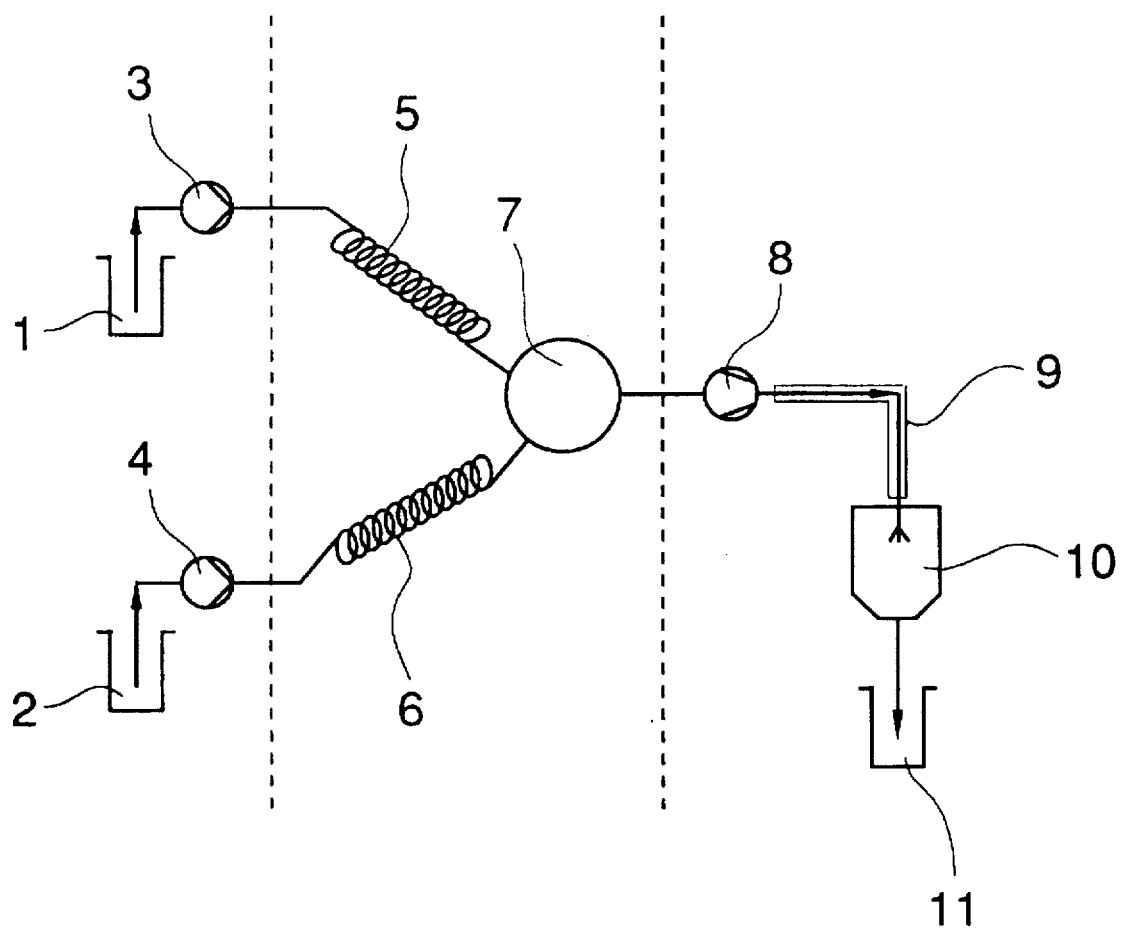

Micronization:

The production of the micronisate is depicted diagrammatically in FIG. 2. The drug solution (1) was initially at 50° C., and the protective colloid solution (2) was initially at 80° C. The drug solution was pumped at 2000 parts/hour by pump (3) through the heat exchanger in an oil bath at 120° C. (5) into the mixing cell (7). The drug solution was mixed in the mixing cell with the protective colloid solution (2) which was pumped by pump (4) at a flow rate of 9000 parts/hour and passed through an exchanger (6) at 130° C. The temperature of the mixture reached 92° C., which is above the melting point of fenofibrate (80° C.). The resulting emulsion was discharged through the pressure-limiting valve (8), conveyed through the heated tube (9) directly into the spray tower (10) and dried therein with inlet air at 160° C. and an outlet temperature of 80° C. This resulted in a free-flowing powder (11) which on dispersion in water afforded a colloidal dispersion of fenofibrate with a particle size of 0.66 μm (volume average, determined by laser diffraction).

EXAMPLE 3

Production of a micronisate of levemopamil hydrochloride

Drug dispersion:

9 g of levemopamil•HCl were dispersed with 1.8 g of ascorbyl palmitate in a mixture of 31.7 g of isopropanol and 4.3 g of water.

Protective colloid solution:

A solution of 15 g of gelatin type B, 100 Bloom and 22.5 g of lactose in one liter of water was adjusted to pH 11.4 with NaOH.

Micronization:

The production of the micronisate is depicted diagrammatically in FIG. 1. The drug dispersion (1) was pumped at 0.55 kg/h by pump (3) into the first mixing cell (6) in which it was mixed with a 1 kg/h stream of water, which had previously been heated to 210° C. by thermostat (5), from vessel (2) via pump (4). The mixing with the hot water resulted in the temperature jumping to 185° C., which exceeds the melting point of levemopamil•HCl (182° C.). After less than 0.5 s at 185° C., the resulting levemopamil•HCl emulsion was mixed in the second mixing cell (7) with the protective colloid solution (8) which was pumped by pump (9) at a flow rate of 9 kg/h. The resulting micronisate was discharged through the pressure-limiting valve (10). Spray-drying of the micronisate resulted in a powder with a drug content of 22.3%. Dissolution of the powder in water resulted in levemopamil•HCl nanoparticles with an average size of 580 nm (measured by dynamic light scattering).

EXAMPLE 4

Production of a micronisate of propafenone•HCl.

Drug dispersion:

As for levemopamil•HCl (Example 3) but with propafenone•HCl.

Protective colloid solution:

As in Example 3 but with pH 11.0.

Production of the micronisate:

The micronisate was produced as described in Example 3. The temperature in the mixing cell (6) was 177° C. and thus above the melting point of propafenone•HCl (174° C.). Spray-drying resulted in a powder with 23.3% drug, and the size of the nanoparticles after redissolution of the powder in water was 350 nm (dynamic light scattering).

EXAMPLE 5

Production of a dispersion of anipamil·HCl nanoparticles
Production of the drug dispersion:

21 g of anipamil·HCl were dispersed with 0.24 g of 10× ethoxylated isononylphenol in 240 g of water.

Preparation of the protective colloid solution:

A solution of 15 g/l gelatin type B, 100 Bloom, was adjusted to pH 9 with NaOH.

Micronization:

| The micronization was carried out as in Example 4 with the following changes: | |
| --- | --- |
| Dispersion pumping rate: | 2 kg/h |
| Water pumping rate: | 4 kg/h |
| Protective colloid solution pumping rate: | 30 kg/h |
| Heat exchanger temperature: | 100° C. |
| 1st mixing cell (6) temperature: | 93° C. |
| Melting point of anipamil-HCl: | 63° C. |

The average size of the anipamil·HCl nanoparticles in the resulting dispersion in water was 220 nm (dynamic light scattering). The drug content in this nanoparticle dispersion was 0.45%.

EXAMPLE 6

Micronization of canthaxanthin
Preparation of the drug dispersion:

21 g of canthaxanthin were dispersed with 4.6 g of ascorbyl palmitate in a mixture of 223 g of water and 12 g of 1M NaOH.

Protective colloid solution prepared as in Example 5.

The micronization was carried out as in Example 4 with the following changes:

| Dispersion pumping rate: | 1.1 kg/h |
| --- | --- |
| Water pumping rate: | 6 kg/h |
| Protective colloid solution pumping rate: | 30 kg/h |
| Heat exchanger temperature: | 240° C. |
| 1st mixing cell (6) temperature: | 223° C. |
| Melting point of canthaxanthin: | 211° C. |

The average size of the canthaxanthin nanoparticles in the resulting dispersion in water was 370 nm (dynamic light scattering). The drug content in the nanoparticle dispersion was 0.21%.

EXAMPLE 7

Production of a micronisate of nesapidil

Preparation of the drug dispersion:

3 g of nesapidil were dispersed with 0.6 g of ascorbyl palmitate in a mixture of 31.7 g of isopropanol and 4.3 g of water.

Protective colloid solution prepared as in Example 5.

Micronization:

| The micronization was carried out as in Example 4 with the following changes: | |
| --- | --- |
| Heat exchanger temperature: | 210° C. |
| 1st mixing cell (6) temperature: | 175° C. |
| Nesapidil melting point: | 164° C. |

Spray-drying resulted in a powder with a nesapidil content of 10.3%. The average particle size after redissolution of the powder in water was 350 nm (dynamic light scattering).

We claim:

1. A process for producing fine-particle, essentially amorphous dye or drug preparations by converting a relatively coarse-particle aqueous dispersion or an organic solution in a solvent dissolving to an extent of at least 10% in water into a colloidal dispersion in water, wherein the aqueous dispersion or organic solution of the dye or drug is subjected to turbulent mixing at a temperature above the melting point of the dye or drug, where appropriate under pressure, with water or an aqueous protective colloid solution, and the resulting melt emulsion is immediately spray-dried or converted into a suspension by cooling.

2. A process as claimed in claim 1, wherein no organic solvent is used.

3. A process as claimed in claim 1, wherein the cooling takes place as quickly as possible after the formation of the hot melt emulsion.

4. A process as claimed in claim 1, wherein water or water/solvent mixture is removed from the resulting suspension to afford an easily redispersable powder.

* * * * *